United States Patent [19]

Sidi et al.

[11] 4,281,178

[45] Jul. 28, 1981

[54] PROCESS FOR THE PRODUCTION OF BENZOIC ACID FROM PROCESS RESIDUES THAT CONTAIN BENZYL BENZOATE

[75] Inventors: Henri Sidi, Paramus; William G. Hughes, Plainfield, both of N.J.

[73] Assignee: Tenneco Chemicals, Inc., Saddle Brook, N.J.

[21] Appl. No.: 141,713

[22] Filed: Apr. 18, 1980

Related U.S. Application Data

[63] Continuation-in-part of Ser. No. 99,696, Dec. 3, 1979, abandoned.

[51] Int. Cl.$^3$ .................... C07C 51/16; C07C 51/255
[52] U.S. Cl. .................................. 562/412; 562/421
[58] Field of Search ............................. 562/412, 421

[56] References Cited

U.S. PATENT DOCUMENTS 2,255,421   9/1941   Groll et al. ........................... 562/494

*Primary Examiner*—Alan Siegel
*Attorney, Agent, or Firm*—Evelyn Berlow

[57] ABSTRACT

Benzoic acid is produced from process residues resulting from the liquid phase air oxidation of toluene by a process in which
 (a) a benzyl benzoate-rich fraction is separated from the spent catalyst and high-boiling reaction by-products in the process residue;
 (b) the benzyl benzoate-rich fraction is contacted with an oxygen-containing gas in the presence of an oxidation catalyst at 130°–200° C./1–10 atmospheres until 25% to 60% of the benzyl benzoate has been oxidized to benzoic acid, and
 (c) benzoic acid is recovered from the oxidation product mixture.

10 Claims, No Drawings

PROCESS FOR THE PRODUCTION OF BENZOIC ACID FROM PROCESS RESIDUES THAT CONTAIN BENZYL BENZOATE

This is a continuation-in-part of our application Ser. No. 99,696, which was filed on Dec. 3, 1979 now abandoned.

This invention relates to a process for the recovery of benzoic acid from process residues and other materials that contain benzyl benzoate. It further relates to a process for the production of benzoic acid by the liquid phase oxidation of benzyl benzoate.

In widely-used industrial processes for the production of benzoic acid and benzaldehyde, toluene is oxidized in the liquid phase with an oxygen-containing gas in the presence of a heavy metal oxidation catalyst to form a product mixture that contains benzaldehyde, benzoic acid, unreacted toluene, and such reaction by-products as benzyl alcohol, benzyl benzoate, benzoic alhydride, diphenyls, and phthalic anhydride. Benzaldehyde and benzoic acid are generally recovered from these product mixtures by distillation and/or crystallization procedures. In one such procedure, the product mixture is distilled to separate a fraction containing benzaldehyde and unreacted toluene from a residue that contains a major amount of benzoic acid and minor amounts of reaction by-products. Benzoic acid is recovered from this residue either by recrystallization from a solvent, such as toluene, or by distillation under vacuum. The distillation residue and the residue remaining after removal of the solvent from the filtrate contain benzoic acid, benzyl benzoate, other reaction by-products having boiling points higher than that of benzaldehyde, such as biphenyl, methylbiphenyl, phthalic anhydride, and benzoic anhydride, and spent catalyst.

While benzyl benzoate can be recovered from such process residues by procedures involving vacuum distillation, it is difficult to obtain benzyl benzoate in the pure state by such procedures because its boiling point is only slightly different from the boiling points of other components of the residues. In addition, the amount of benzyl benzoate that can be marketed is too small to warrant the relatively high cost of the vacuum distillation procedures.

Several procedures have been proposed for the recovery of useful materials from the residues remaining after the separation of benzoic acid and benzaldehyde from product mixtures resulting from the liquid phase air oxidation of toluene, but none has proven to be satisfactory. For example, French Pat. No. 2,376,113 discloses processes in which a tar that contains benzyl benzoate is subjected to hydrolysis or to ammonolysis to convert the benzyl benzoate to benzyl alcohol and either benzoic acid, a salt of benzoic acid, or benzamide, and the resulting mixture is distilled to separate benzyl alcohol from it. These procedures are not economically feasible because of the high capital and operating costs involved. In addition, benzyl alcohol tends to react with the benzoic acid or benzoic acid salts in the hydrolysis mixture to form benzyl benzoate during the distillation unless a means of preventing esterification is employed. The ammonolysis procedure must include an additional step in which the benzamide formed is either recovered or converted to benzoic acid. French Pat. No. 2,376,121 discloses a process in which a process residue that contains benzyl alcohol and benzyl benzoate is subjected to an esterification or transesterification reaction with a carboxylic acid having 1 to 18 carbon atoms, which is preferably acetic acid, propionic acid, or butyric acid, to form a product mixture that contains the benzyl esters of the added acid and benzoic acid. These benzyl esters are then recovered. This process, which is costly to carry out, yields products, such as benzyl benzoate, benzyl acetate, and benzyl butyrate, that have limited commercial value.

In the absence of a suitable economical procedure for separating and recovering their components, the benzyl benzoate-containing tars and other process residues are ordinarily incinerated.

In accordance with this invention, it has been found that benzoic acid can be produced efficiently and economically by the liquid phase oxidation of a feedstock that is either benzyl benzoate or a tar or other process residue that comprises benzyl benzoate.

In a preferred embodiment of the invention, the feedstock that is subjected to liquid phase oxidation to convert benzyl benzoate to benzoic acid is obtained from a tar or other residue resulting from a process in which toluene is oxidized with an oxygen-containing gas in the liquid phase in the presence of a heavy metal oxidation catalyst to produce an oxidation product mixture, and benzaldehyde and/or benzoic acid is recovered from the oxidation product mixture.

Because the spent catalyst and certain high-boiling reaction by-products in the process residues resulting from the liquid phase oxidation of toluene will interfere with the oxidation of benzyl benzoate to benzoic acid, the residues must be fractionated to separate a benzyl benzoate-rich fraction from a residue that contains spent catalyst and high-boiling impurities before the oxidation reaction is carried out. This separation can be effected, for example, by heating the process residue to a temperature in the range of 180° C. to 250° C. at a pressure in the range of 50 to 200 torr to separate a benzyl benzoate-rich fraction from a residue that contains spent catalyst and high-boiling by-products of the toluene oxidation reaction. The benzyl benzoate-rich fraction is then contacted with an oxygen-containing gas in the presence of an oxidation catalyst to convert benzyl benzoate to benzoic acid.

In the process of this invention, the benzyl benzoate-rich fraction that has been separated from the catalyst and high-boiling reaction by-products in a toluene oxidation process residue or another benzyl benzoate feedstock is introduced into a reaction vessel. An oxygen-containing gas, which is usually air, is fed into the bottom of the reaction vessel and allowed to bubble through the feedstock. The oxidation of benzyl benzoate to benzoic acid is effected in the presence of an oxidation catalyst that is a cobalt, manganese, or vanadium salt of a monocarboxylic acid having 1 to 12 carbon atoms, such as cobalt acetate, cobalt octoate, cobalt dodecanoate, cobalt naphthenate, cobalt benzoate, manganese acetate, manganese octoate, or vanadium octoate. The amount of the oxidation catalyst that is used is in the range of 0.01% to 3%, based on the weight of benzyl benzoate in the feedstock. Best results have been obtained when 0.05% to 1% of catalyst, based on the weight of benzyl benzoate in the feedstock, was used. The amount of oxygen-containing gas that is used is not critical provided that sufficient oxygen is present to convert the benzyl benzoate to benzoic acid.

The oxidation reaction is carried out at a temperature in the range of 130° C. to 200° C. at a pressure that is sufficient to maintain liquid phase reaction conditions, that is, 1 atmosphere to 10 atmospheres; it is preferably carried out at a temperature in the range of 150° C. to 175° C. at a pressure in the range of 1 atmosphere to 5 atmospheres. The oxidation reaction is usually discontinued when about 25% to 60% of the benzyl benzoate has been oxidized to benzoic acid because beyond this conversion level the reaction takes place too slowly to be useful commercially. Benzoic acid can be recovered from the oxidation mixture by vacuum distillation or by crystallization procedures. Unreacted benzyl benzoate can be separated from the oxidation mixture by distillation or other suitable procedures, or the oxidation mixture from which benzoic acid has been recovered can be discarded.

While the process of this invention is of particular value for the production of benzoic acid from process residues that result from the catalytic liquid phase oxidation of toluene and that contain benzyl benzoate, it can also be used to produce benzoic acid from commercial benzyl benzoate or from other materials that contain benzyl benzoate.

The oxidation of benzyl benzoate to benzoic acid by the process of this invention may be carried out in a batchwise, semi-continuous, or continuous manner.

The invention is further illustrated by the following examples. In these examples, all parts are parts by weight and all percentages are percentages by weight.

EXAMPLE 1

A. The liquid reaction product resulting from the liquid phase air oxidation of toluene in the presence of cobalt octoate was cooled to crystallize benzoic acid from it. After separation of the crystallized benzoic acid from it, the filtrate was distilled first at atmospheric pressure and then at a pressure of 100 torr to remove toluene, benzaldehyde, most of the remaining benzoic acid, and low-boiling reaction by-products from a tarry residue that contained 8.7% benzoic acid, 75.1% benzyl benzoate, and 3.5% benzoic anhydride as well as spent catalyst and high-boiling reaction by-products.

B. Five hundred parts of the tarry residue was charged into a flask equipped with a thermometer, boiling chips, an electrically-heated Claisen head, and a heating mantle. The Claisen head was connected to a flask which in turn was connected to a vacuum pump. This system was equipped with a T-tube, which made possible an artificial air leak.

The tarry residue was heated under vacuum to separate 397.1 parts of a distillate that had a boiling range of 204° C.–245° C./140–150 torr and that contained 16.4% benzoic acid, 82.0% benzyl benzoate, and 1.6% benzoic anhydride from 102.6 parts of tars residue that contained 4.5% benzoic acid, 7.7% benzyl benzoate, and 0.73% cobalt.

C. To a flask equipped with stirrer, thermometer, condenser, and air inlet tube were charged 253.4 parts of the benzyl benzoate-rich distillate and 1.0 part of 12% cobalt octoate solution. The reaction mixture was stirred and heated at 170° C.–175° C. under atmospheric pressure while air was passed under its surface at the rate of 1 cubic foot/hour for 12 hours. The reaction mixture solidified when its was cooled to room temperature.

There was obtained 252.2 parts of an oxidation product that contained 31.4% benzoic acid, 59.9% benzyl benzoate, and small amounts of benzaldehyde, phthalic anhydride, diphenyl, and other reaction by-products. This product was distilled under vacuum to separate a benzoic acid fraction and a benzyl benzoate fraction from the catalyst-containing residue. The benzyl benzoate fraction was recycled to the oxidation step of the process.

EXAMPLE 2

The procedure described in Example 1 was repeated using in Step A a tarry residue that contained 46% benzoic acid, 45% benzyl benzoate, 6% benzoic anhydride, and 3% catalyst and higher-boiling reaction by-products.

This residue was distilled under vacuum to separate a benzoic acid fraction and then a fraction that contained 83.4% benzyl benzoate, 8.7% benzoic acid, 6.4% benzoic anhydride, and small amounts of reaction by-products from a residue that contained high-boiling reaction by-products, spent catalyst, and small amounts of benzoic acid and benzyl benzoate.

The distillate was stirred and heated at 150° C.–155° C. under a pressure of 5 atmospheres while air was bubbled through it for 10 hours. The reaction mixture solidified when it was cooled to room temperature.

There was obtained an oxidation product that contained 51% benzoic acid, 47% benzyl benzoate, and small amounts of reaction by-products. Benzoic acid and benzyl benzoate fractions were separated from the oxidation product, and the benzyl benzoate fraction was recycled to the oxidation step of the process.

EXAMPLE 3

A mixture of 250 parts of commercial benzyl benzoate (99%+ purity) and 1 part of 12% cobalt octoate solution was stirred and heated at 165° C.–170° C. under atmospheric pressure while air was passed through it at the rate of 1 cubic foot/hour for 12 hours. The reaction mixture solidified when it was cooled to room temperature. There was obtained 250.3 parts of an oxidation product that contained 39.1% benzoic acid, 59.6% benzyl benzoate, 0.5% benzaldehyde, 0.5% diphenyl, 0.1% phthalic anhydride, and 0.2% other reaction by-products.

The oxidation product was distilled at a pressure of 100 torr to separate fractions that consisted of substantially pure benzoic acid and benzyl benzoate from the residue tat contained the catalyst and higher boiling reaction by-products.

EXAMPLE 4

A mixture of 250 parts of commercial benzyl benzoate and 1 part of 6% cobalt octoate solution was stirred and heated at 150° C.–160° C. under atmospheric pressure while air was passed through it at the rate of 1 cubic foot/hour for 14 hours. The reaction mixture solidified when it was cooled to room temperature. There was obtained 253 parts of an oxidation product that contained 43.1% benzoic acid, 51.7% benzyl benzoate, 3.5% benzaldehyde, and 1.7% other reaction by-products.

The oxidation product was distilled under vacuum to separate fractions that consisted of substantially pure benzoic acid and benzyl benzoate from the residue that contained the catalyst and higher-boiling reaction by-products.

What is claimed is:

1. In the process for the production of benzoic acid by the liquid phase oxidation of toluene with an oxygen-containing gas in the presence of a heavy metal oxidation catalyst wherein benzoic acid and benzaledehyde are separated from a process residue that comprises benzoic acid, benzyl banzoate, reaction by-products having boiling points higher than the boiling point of benzaldehyde, and spent catalyst, the improvement that comprises the steps of
  (a) heating the process residue to a temperature in the range of 180° C. to 250° C. at a pressure in the range of 50 to 200 torr to separate a benzyl benzoate-rich fraction from a residue that contains spent catalyst and the higher-boiling by-products of the toluene-oxidation reaction;
  (b) contacting the benzyl benzoate-rich fraction with an oxygen-containing gas in the presence of an oxidation catalyst selected from the group consisting of cobalt, manganese, and vanadium salts of monocarboxylic acids having 1 to 12 carbon atoms at a temperature in the range of 130° C. to 200° C. at a pressure in the range of 1 atmosphere to 10 atmospheres until 25% to 60% of the benzyl benzoate has been oxidized to benzoic acid and an oxidation product mixture that comprises benzoic acid and benzyl benzoate has been formed; and
  (c) recovering benzoic acid from the oxidation product mixture.

2. The process of claim 1 wherein in Step (b) the oxygen-containing gas is air.

3. The process of claim 1 wherein in Step (b) the oxidation is carried out at a temperature in the range of 150° C to 175° C. at a pressure in the range of 1 atmosphere to 5 atmospheres.

4. The process of claim 1 wherein in Step (b) 0.01% to 3%, based on the weight of benzyl benzoate, of the oxidation catalyst is used.

5. The process of claim 1 wherein in Step (b) 0.05% to 1%, based on the weight of benzyl benzoate, of cobalt octoate is used as the oxidation catalyst 6. The process of claim 1 wherein the residue remaining after Step (c) is recycled to Step (a).

7. The process for the production of benzoic acid that comprises contacting benzyl benzoate with an oxygen-containing gas in the presence of an oxidation catalyst selected from the group consisting of cobalt, manganese, and vanadium salts of monocarboxylic acids having 1 to 12 carbon atoms at a temperature in the range of 130° C. to 200° C. at a pressure in the range of 1 atmosphere to 10 atmospheres until 25% to 60% of the benzyl benzoate has been oxidized to benzoic acid and recovering the benzoic acid formed.

8. The process of claim 7 wherein the oxidation of benzyl benzoate is carried out at a temperature in the range of 150° C. to 175° C. at a pressure in the range of 1 atmosphere to 5 atmospheres.

9. The process of claim 7 wherein the oxygen-containing gas is air.

10. The process of claim 7 wherein 0.05% to 1%, based on the weight of benzyl benzoate, of cobalt octoate is used as the oxidation catalyst.

* * * * *